United States Patent
Horii (10) Patent No.: US 9,005,453 B2
(45) Date of Patent: Apr. 14, 2015

(54) DETECTION TARGET SUBSTANCE DETECTING METHOD, DETECTION TARGET SUBSTANCE DETECTING CHIP USED IN THE METHOD, AND DETECTION TARGET SUBSTANCE DETECTING APPARATUS

(71) Applicant: FUJIFILM Corporation, Tokyo (JP)

(72) Inventor: Kazuyoshi Horii, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 275 days.

(21) Appl. No.: 13/971,067

(22) Filed: Aug. 20, 2013

(65) Prior Publication Data

US 2013/0337475 A1  Dec. 19, 2013

Related U.S. Application Data

(63) Continuation of application No. PCT/JP2012/001099, filed on Feb. 20, 2012.

(30) Foreign Application Priority Data

Feb. 21, 2011  (JP) .................................. 2011-034297

(51) Int. Cl.
| | |
|---|---|
| B01L 3/00 | (2006.01) |
| B01F 11/02 | (2006.01) |
| G01N 21/63 | (2006.01) |
| B01F 13/00 | (2006.01) |
| G01N 33/543 | (2006.01) |

(52) U.S. Cl.
CPC ............ *G01N 21/63* (2013.01); *B01L 3/50273* (2013.01); *B01L 3/502761* (2013.01); *B01L 3/502715* (2013.01); *B01L 2400/0433* (2013.01);

(Continued)

(58) Field of Classification Search
CPC ................... B01L 3/50273; B01L 2400/0439; B01L 2300/0877; B01L 2400/0436; B01L 3/502715; B01F 13/0059; B01F 2215/0037
USPC .................. 210/748.05; 422/69; 436/518
See application file for complete search history.

(56) References Cited

U.S. PATENT DOCUMENTS

| | | |
|---|---|---|
| 4,575,485 A | 3/1986 | Sizto et al. |
| 2009/0169428 A1 | 7/2009 | Gillespie et al. |
| 2011/0244594 A1 | 10/2011 | Horii |

FOREIGN PATENT DOCUMENTS

| | | |
|---|---|---|
| JP | 6-54315 B2 | 7/1994 |
| JP | 10-267927 A | 10/1998 |
| JP | 2011-214999 A | 10/2011 |

OTHER PUBLICATIONS

International Search Report Issued in PCT/JP2012/001099, mailed on Apr. 24, 2012.

*Primary Examiner* — Melanie Y Brown
*Assistant Examiner* — Erik B Crawford
(74) *Attorney, Agent, or Firm* — Birch, Stewart, Kolasch & Birch, LLP (57) ABSTRACT

Expedient and sensitive detection of a detection target substance is enabled in target substance detection that detects the detection target substance at a sensor portion provided within a flow channel. A detection target substance detecting method for a detecting detection target substance which may be contained in a liquid sample emits ultrasonic waves that propagate in a direction transverse to a flow channel when the liquid sample flows within a ultrasonic wave emission region at which ultrasonic waves can be emitted, to concentrate the detection target substance at a wall surface of the flow channel toward the side of the sensor portion and to detect the detection target substance.

17 Claims, 3 Drawing Sheets

(52) U.S. Cl.
CPC .. *B01L 2400/0436* (2013.01); *B01L 2400/0439* (2013.01); *B01L 2300/0877* (2013.01); *B01F 11/0283* (2013.01); *B01F 13/0059* (2013.01); *B01F 11/02* (2013.01); *B01F 11/0258* (2013.01); *G01N 33/54393* (2013.01)

DETECTION TARGET SUBSTANCE DETECTING METHOD, DETECTION TARGET SUBSTANCE DETECTING CHIP USED IN THE METHOD, AND DETECTION TARGET SUBSTANCE DETECTING APPARATUS

CROSS-REFERENCE TO RELATED APPLICATIONS

This application is a continuation of PCT International Application No. PCT/JP2012/001099 filed on Feb. 20, 2012, which claims priority under 35 U.S.C 119(a) to Application No. 2011-034297 filed Feb. 21, 2011 in Japan, all which are hereby expressly incorporated by reference in the present application.

TECHNICAL FIELD

The present invention is related to a detection target substance detecting method that employs a detecting chip having fine flow channels, the detecting chip employed in the detection target substance detecting method, and a detection target substance detecting apparatus.

BACKGROUND ART

Presently, analysis and quantification of biological substances such as sugars, proteins, and nucleic acids is being performed daily in a wide range of fields, such as clinical examinations, food inspection, and environmental inspections. There are various types of biological substance analysis and quantification methods according to the types of biological substances which are the targets of analysis and quantification. Some of these methods utilize reactions between biological substances and substances that have affinities for the biological substances. For example, quantification methods that utilize antigen antibody reactions are established as highly sensitive and reliable immunoassay methods, and are commonly used in a wide range of fields such as clinical examinations. However, if commercially available reagent kids are employed, each of the multitude of reactions take time, and expedient tests are difficult when there are great amounts of samples. This is because the kinetic energy at a specific temperature controls the reaction speed by the frequency at which molecules collide with each other.

For example, in antigen antibody reactions in which one of the antigens and the antibodies are immobilized, the molecular collision frequency becomes extremely low, and the reaction speed also decreases correspondingly. Use of ultrasonic waves during reactions in order to increase reaction speeds has been described in Patent Documents 1 through 3, as a solution to resolve this issue. In the methods disclosed in these documents, it is considered that the ultrasonic waves operate on the antigens or the antibodies which are not immobilized, to increase the collision frequency thereof with respect to the immobilized antibodies or antigens, to promote binding reactions.

PCT Japanese Publication No. 6(1994)-054315 and Japanese Unexamined Patent Publication No. 10(1998)-267927 disclose inventions in which molecular vibrations are caused by ultrasonic waves to increase collision rates thereof with surrounding substances, thereby increasing reaction speeds. Further, the invention of Japanese Unexamined Patent Publication No. 10(1998)-267927 is characterized by modulating the frequency of the ultrasonic waves to disrupt the state of vibration, to cause translational movement over a wider range. U.S. Patent Application Publication No. 20090169428 discloses a method for detecting biological substances using flow channels, in which ultrasonic standing waves are generated within flow channels such that the nodes thereof are positioned at a detecting surface, to concentrate particles within the flow channels at the positions of the nodes of the standing waves.

DISCLOSURE OF THE INVENTION

However, in the methods of PCT Japanese Publication No. 6(1994)-054315 and Japanese Unexamined Patent Publication No. 10(1998)-267927, there is a problem that reaction speed is not improved when the concentration of immune substances is low even if the immune substances are caused to vibrate, because the amount of other immune substances in the vicinities thereof is low. In addition, in such low concentration situations, the amount of immune substance that can be detected at a sensor portion depends on the dispersion speed of the substance. Therefore, it is considered that a great improvement in detection sensitivity cannot be expected. Further, in the case that one of antibodies and antigens are immobilized in antigen antibody reactions, if the antibodies or antigens which are immobilized are merely caused to vibrate, the vibrating antibodies or antigens merely move reciprocally within a given region, and the improvement in molecular collision frequency is limited as a result. In addition, in the method of U.S. Patent Application Publication No. 20090169428, stringent control of the widths of the flow channels or frequency are necessary to generate standing waves within the flow channels, and it is extremely difficult to generate the standing waves themselves. Further, even if the standing waves are generated, the detecting surfaces become free ends, and therefore there is a problem that the positions of the nodes will be ¼ wavelength away from the detecting surfaces.

The present invention has been developed in view of the foregoing problems. It is an object of the present invention to provide a detection target substance detecting method that enables expedient and sensitive detection of a detection target substance in target substance detection that detects the detection target substance at a sensor portion provided within a flow channel, a detection target substance detecting chip which is employed in the detection target substance detecting method, and a detection target substance detecting apparatus.

A detection target substance detecting method of the present invention that achieves the above objective is a detection target substance detecting method for detecting a detection target substance which may be contained in a liquid sample, comprising:

employing a detecting chip equipped with: a flow channel member having a flow channel through which the liquid sample is caused to flow; a sensor portion formed at a first predetermined region on a wall surface of the flow channel, at which an immobilized binding substance that specifically binds with the detection target substance is immobilized; and an acoustic absorber provided at a predetermined portion of the flow channel member corresponding to the first predetermined region and/or at a predetermined portion of the flow channel member corresponding to a second predetermined region upstream of the first predetermined region along the flow channel;

causing the liquid sample and an amount of a labeling binding substance that contains a labeling substance, which is to be immobilized onto the sensor portion, corresponding to the amount of the detection target substance to flow into the flow channel;

emitting ultrasonic waves toward the acoustic absorber in a direction perpendicular to the longitudinal direction of the flow channel when the liquid sample passes through an ultrasonic wave emission region at which ultrasonic waves can be emitted;

emitting a measuring light beam onto the sensor portion;

detecting signal light generated by the labeling substance as a result of emission of the measuring light beam; and measuring the amount of the labeling binding substance immobilized onto the detecting surface based on the amount of the signal light, to detect the detection target substance.

In the present specification, the expression "detect the detection target substance" refers to both qualitatively detecting the presence or absence of the detection target substance and quantitatively detecting the amount of the detection target substance.

The expression "a second predetermined region upstream of the first predetermined region along the flow channel" refers to a predetermined region on the wall surface of the flow channel on the side of the wall surface at which the first predetermined region is provided and upstream of the first predetermined region. In other words, the second predetermined region is a region of the wall surface of the flow channel having a positional relationship with the first predetermined region such that when molecules within the liquid sample pass through the vicinity of the second predetermined region, the molecules will pass through the vicinity of the first predetermined region accompanying the flow of the liquid sample.

That the acoustic absorber is "provided at a predetermined portion of the flow channel member corresponding to the first predetermined region and/or at a predetermined portion of the flow channel member corresponding to a second predetermined region upstream of the first predetermined region along the flow channel" includes a case in which the acoustic absorber is provided only at a predetermined portion of the flow channel member corresponding to the first predetermined region, a case in which the acoustic absorber is provided only at a predetermined portion of the flow channel member corresponding to the second predetermined region, and a case in which the acoustic absorber is provided to straddle the two predetermined portions.

The "labeling binding substance" refers to a labeling substance for performing target substance detection by the sandwich method or the competition method, in which one of a pair of substances that specifically bind with each other has surface modifications. The other of the pair of substances is the detection target substance or the immobilized binding substance.

In the detection target substance detecting method of the present invention, it is preferable for the acoustic absorber to be provided at a predetermined portion corresponding to the second predetermined region.

Further, a detection target substance detecting chip of the present invention comprises:

a flow channel member having a flow channel through which a liquid sample that may contain a detection target substance is caused to flow, a flow inlet through which the liquid sample is caused to flow into the flow channel, and an air opening for causing the liquid samples which have flowed in through the flow inlet to flow into the flow channel;

a sensor portion formed at a first predetermined region on a wall surface of the flow channel, at which an immobilized binding substance that specifically binds with the detection target substance is immobilized;

and an acoustic absorber provided at the first predetermined region and/or at a predetermined portion corresponding to a second predetermined region upstream of the first predetermined region along the flow channel.

It is preferable for the detection target substance detecting chip of the present invention to further comprise:

an ultrasonic wave emission portion at which ultrasonic waves are emitted toward the acoustic absorber in a direction perpendicular to the longitudinal direction of the flow channel.

It is preferable for the detection target substance detecting chip of the present invention to further comprise:

an acoustic matching layer provided at least at one of a position between the acoustic absorber and the flow channel and a position between the ultrasonic wave emission portion and the flow channel.

In the detection target substance detecting chip of the present invention, it is preferable for:

the flow channel member to have a recess into which the ultrasonic wave emission portion can be fitted.

It is preferable for the detection target substance detecting chip of the present invention to further comprise:

a labeling binding substance which is provided at a location where it is capable of being mixed with the liquid sample prior to the liquid sample reaching the sensor portion; wherein:

the labeling binding substance comprises one of a first modifying binding substance that specifically binds with the detection target substance and a second modifying binding substance that competes with the detection target substance to specifically bind with the immobilized binding substance, and a labeling substance modified by the one of the first modifying binding substance and the second modifying binding substance.

In this case, the location where the labeling binding substance is capable of being mixed with the liquid sample may be on the wall surface of the flow channel upstream of the second predetermined region, a second flow channel provided in the flow channel member independent of the flow channel, or a container portion provided in the flow channel member independent of the flow channel.

Further, a detection target substance detecting kit of the present invention comprises:

a detection target substance detecting chip comprising: a flow channel member having a flow channel through which a liquid sample that may contain a detection target substance is caused to flow, a flow inlet through which the liquid sample is caused to flow into the flow channel, and an air opening for causing the liquid samples which have flowed in through the flow inlet to flow into the flow channel; a sensor portion formed at a first predetermined region on a wall surface of the flow channel, at which an immobilized binding substance that specifically binds with the detection target substance is immobilized; and an acoustic absorber provided at the first predetermined region and/or at a predetermined portion corresponding to a second predetermined region upstream of the first predetermined region along the flow channel; and a labeling solution that includes a labeling binding substance for labeling the detection target substance;

the labeling binding substance comprising one of a first modifying binding substance that specifically binds with the detection target substance and a second modifying binding substance that competes with the detection target substance to specifically bind with the immobilized binding substance, and a labeling substance modified by the one of the first modifying binding substance and the second modifying binding substance.

A detection target substance detecting apparatus of the present invention is that which is utilized in a detection target substance detecting method that employs a detection target substance detecting chip comprising: a flow channel member having a flow channel through which a liquid sample that may contain a detection target substance is caused to flow, a flow inlet through which the liquid sample is caused to flow into the flow channel, and an air opening for causing the liquid samples which have flowed in through the flow inlet to flow into the flow channel; a sensor portion formed at a first predetermined region on a wall surface of the flow channel, at which an immobilized binding substance that specifically binds with the detection target substance is immobilized; and an acoustic absorber provided at the first predetermined region and/or at a predetermined portion corresponding to a second predetermined region upstream of the first predetermined region along the flow channel, comprising:

ultrasonic wave emitting means for emitting ultrasonic waves toward the acoustic absorber in a direction perpendicular to the longitudinal direction of the flow channel;

light emitting means for emitting a measuring light beam to the sensor portion; and a photodetector for detecting signal light generated at the sensor portion due to the measuring light beam being emitted thereon.

The detection target substance detecting method of the present invention employs the detecting chip equipped with the flow channel member having the flow channel through which the liquid sample flows, the sensor portion, and the acoustic absorber. The liquid sample and an amount of the labeling binding substance that contains the labeling substance, which is immobilized onto the sensor portion, corresponding to the amount of the detection target substance are caused to flow in the flow channel. When the liquid sample passes through the ultrasonic wave emission region at which ultrasonic waves can be emitted, ultrasonic waves are emitted toward the acoustic absorber in a direction perpendicular to the longitudinal direction of the flow channel. The measuring light beam is emitted onto the sensor portion, and signal light generated by the labeling substance due to the emission of the measuring light beam is detected. The amount of the labeling binding substance immobilized on the sensor portion is measured based on the amount of the detected signal light, to detect the detection target substance. Because the ultrasonic wave is emitted toward the acoustic absorber that absorbs ultrasonic waves in the direction perpendicular to the longitudinal direction of the flow channel, forces imparted by radiant pressure of the ultrasonic waves act on substances within the flow channel. The forces operate in the direction that the ultrasonic waves propagate. Therefore, the forces promote movement of substances within the flow channel toward the vicinity of the first predetermined region and/or the vicinity of the second predetermined region. Accordingly, substances within the flow channel become concentrated at the vicinity of the first predetermined region and/or the vicinity of the second predetermined region, and flow to the vicinity of the sensor portion in a concentrated state. The number of collisions between the detection target substance and the immobilized binding substance increases at the sensor portion, and reaction speeds therebetween are improved. As a result, expedient and sensitive detection of the detection target substance becomes possible in target substance detection that detects a detection target substance at a sensor portion provided in a flow channel.

Further, the detection target substance detecting chip comprises the flow channel member having the flow channel through which the liquid sample that may contain the detection target substance is caused to flow, the flow inlet through which the liquid sample is caused to flow into the flow channel, and the air opening for causing the liquid samples which have flowed in through the flow inlet to flow into the flow channel; the sensor portion formed at the first predetermined region on the wall surface of the flow channel, at which the immobilized binding substance that specifically binds with the detection target substance is immobilized; and the acoustic absorber provided at the first predetermined region and/or at the predetermined portion corresponding to the second predetermined region upstream of the first predetermined region along the flow channel. The above detection target substance detecting method can be executed by the chip having this configuration. As a result, expedient and sensitive detection of the detection target substance becomes possible in target substance detection that detects a detection target substance at a sensor portion provided in a flow channel.

Further, the detection target substance detecting apparatus of the present invention comprises: the detection target substance detecting chip comprising the flow channel member having the flow channel through which the liquid sample that may contain the detection target substance is caused to flow, the flow inlet through which the liquid sample is caused to flow into the flow channel, and the air opening for causing the liquid samples which have flowed in through the flow inlet to flow into the flow channel; the sensor portion formed at the first predetermined region on the wall surface of the flow channel, at which the immobilized binding substance that specifically binds with the detection target substance is immobilized; and the acoustic absorber provided at the first predetermined region and/or at the predetermined portion corresponding to the second predetermined region upstream of the first predetermined region along the flow channel; the ultrasonic wave emitting means provided on the flow channel member that emits ultrasonic waves toward the acoustic absorber in a direction perpendicular to the longitudinal direction of the flow channel; the light emitting means for emitting the measuring light beam onto the sensor portion; and the photodetector for detecting the signal light generated at the sensor portion due to emission of the measuring light beam. The above detection target substance detecting method can be executed by the apparatus having this configuration. As a result, expedient and sensitive detection of the detection target substance becomes possible in target substance detection that detects a detection target substance at a sensor portion provided in a flow channel.

BEST MODE FOR CARRYING OUT THE INVENTION

Hereinafter, embodiments of the present invention will be described with reference to the attached drawings. However, the present invention is not limited to the embodiments to be described below. Note that the dimensions of the elements in the drawings differ from the actual dimensions thereof, to facilitate visual understanding.

[First Embodiment]

Figure 1A:
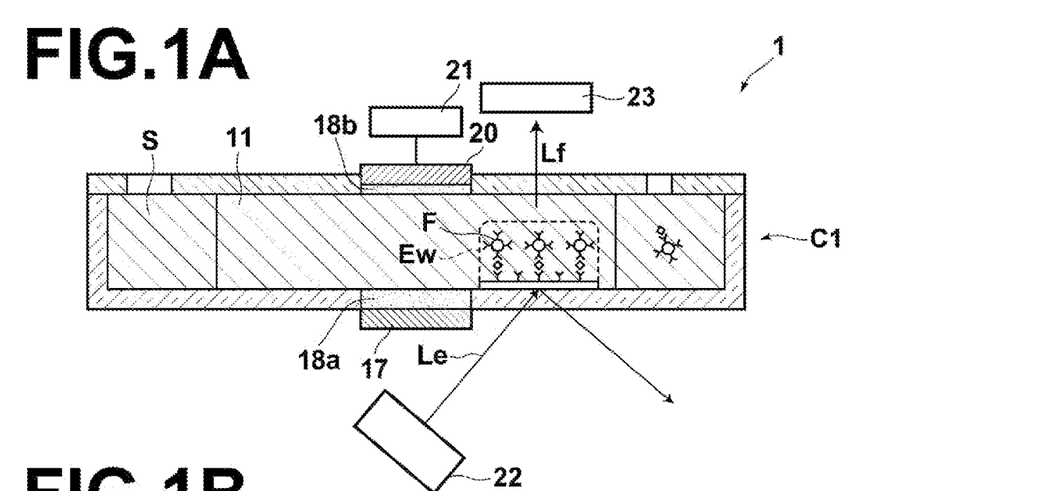
FIG. 1A is a schematic sectional diagram that illustrates a detection target substance detecting apparatus employed to execute a detection target substance detecting method according to a first embodiment of the present invention.
Figure 1B:
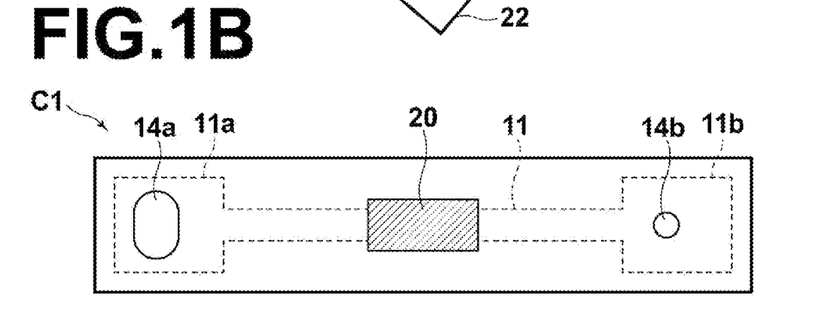
FIG. 1B is a schematic plan view that illustrates a detection target substance detecting chip and an ultrasonic wave emitting section employed to execute the detection target substance detecting method according to the first embodiment of the present invention.
Figure 1C:
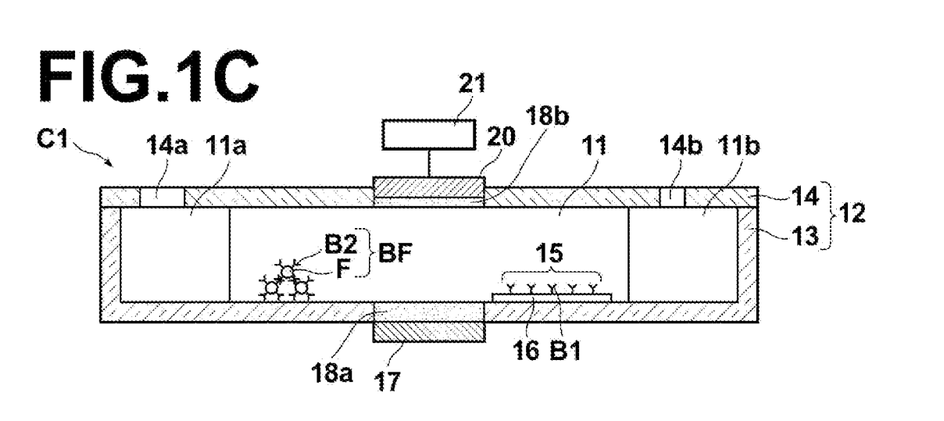
FIG. 1C is a schematic sectional view that illustrates the detection target substance detecting chip and the ultrasonic wave emitting section employed to execute the detection target substance detecting method according to the first embodiment of the present invention.
Figure 2:
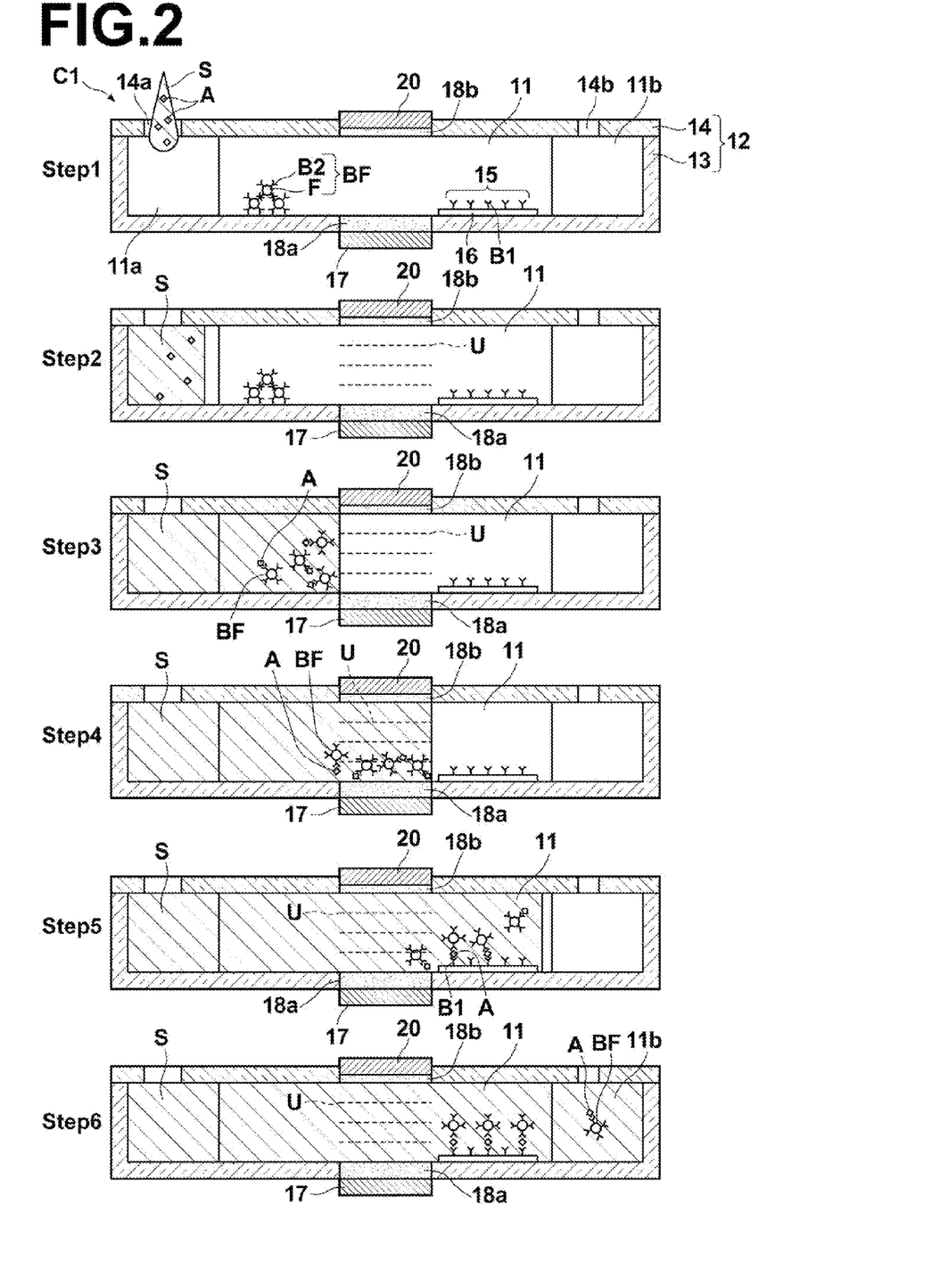
FIG. 2 is a collection of schematic sectional diagrams that illustrate the steps of an immunological examination performed by the sandwich method using the detection target substance detecting method according to the first embodiment of the present invention.

First simply as "detecting chip"), and a detection target substance detecting apparatus (hereinafter, also referred to simply as "detecting apparatus") according to a first embodiment will be described. FIG. 1A is a schematic sectional diagram that illustrates a detecting apparatus 1 employed to execute the detecting method according to the present embodiment. FIG. 1B is a schematic plan view that illustrates a detecting chip C1 and an ultrasonic wave emitting section 20 employed in the detecting method of the present embodiment. FIG. 10 is a schematic sectional view that illustrates the detecting chip C1 and the ultrasonic wave emitting section 20 and 21 employed in the detecting method according to the present embodiment. FIG. 2 is a collection of schematic sectional diagrams that illustrate the steps of an immunological examination performed by the sandwich method using the detection target substance detecting method according to the present embodiment. Note that the present embodiment will be described as a case in which antigens and antibodies are employed as pairs of substances that specifically bind with each other. More specifically, the present embodiment will be described as a case in which the detection target substance is an antigen, the substance that specifically binds with the detection target substance is an antibody, and antigens which may be contained in a whole blood sample (liquid sample) are detected by the sandwich method that employs fluorescent labels.

As illustrated in FIG. 1A, the detecting method of the present embodiment is executed employing the detecting apparatus 1 equipped with: the detecting chip C1; the ultrasonic wave emitting section 20 provided upstream from the sensor portion 15 that emits ultrasonic waves U toward an acoustic absorber 17 in a direction (the vertical direction in the drawing sheet of FIG. 1A) perpendicular to the longitudinal direction of a flow channel 11 (the horizontal direction in the drawing sheet of FIG. 1A) through the flow channel 11; the ultrasonic wave controlling section 21 that controls the ultrasonic wave emitting section 20; a light source 22; and a photodetector 23. The detecting chip C1 includes a flow channel member 12 having the flow channel 11, a flow inlet 14a through which a liquid sample is caused to flow into the flow channel 11, and an air opening 14b for causing the liquid sample which has flowed in through the flow inlet 14a to flow into the flow channel 11; the sensor portion 15 formed at a first predetermined region on the wall surface of the flow channel 11; the acoustic absorber 17 provided at a predetermined portion of the flow channel member 12 corresponding to a second predetermined region upstream of the first predetermined region; and fluorescent labeling antibodies BF provided in a dry state upstream of the second predetermined region 15.

Specifically, the detecting method of the present embodiment employs the detecting apparatus 1 to cause a whole blood sample S that may contain antigens A to flow into the flow channel 11. The whole blood sample S is caused to contact the fluorescent labeling antibodies BF. When the liquid sample and the fluorescent labeling antibodies BF flow along the flow channel and pass an ultrasonic wave emission region at which emission of ultrasonic waves is enabled, the ultrasonic waves U are emitted toward the acoustic absorber 17 in a direction that traverses the flow channel 11. A measuring light beam Le is emitted toward the sensor portion 15 using the light source 22. After the whole blood sample S that flows through the flow channel 11 reaches the sensor portion 15, fluorescence Lf generated by the fluorescent labeling antibodies BF due to emission of the measuring light beam Le is detected by the photodetector 23. The amount of the fluorescent labeling antibodies BF immobilized on the sensor portion 15 is measured based on the amount of detected fluorescence Lf, to detect the antigens A. At this time, in the case that the whole blood sample S contains the antigens A, the fluorescent labeling antibodies BF bind with the antigens A, and the fluorescent labeling antibodies BF bind to immobilized antibodies B1, which are immobilized on the sensor portion 15, via the antigens A.

The detecting chip C1 is basically constituted by the flow channel member 12 having the flow channel, the sensor portion 15 within the flow channel, and the acoustic absorber 15.

The flow channel member 12 includes a lower plate member 13 having a U shaped groove, and an upper plate member 14 that covers the groove. The lower plate member 13 and the upper plate member 15 are joined by ultrasonic welding, for example. It is preferable for the lower plate member 13 and the upper plate member 14 to be injection molded resin. In this case, polymethyl methacrylate (PMMA), polycarbonate (PC), non crystalline polyolefin (APO) that includes cycloolefin, polystyrene, and Zeonex™ are particularly preferred. Liquid reservoirs 11a and 11b for injection and for discharge are respectively provided at the ends of the flow channel 11. A flow inlet 14a, which is connected to the liquid reservoir 11a for injecting liquids and functions to inject fluids therein, and an air opening 14b, which is connected to the liquid reservoir 11b for discharging liquids and functions to suction air therefrom, are formed in the upper plate member 14. The upper plate member 14 is joined with the lower plate member 13 by ultrasonic welding or the like after a metal film 16 is formed. The flow channel member 12 has a recess into which the ultrasonic wave emitting section 20 can be fitted. Thereby, the position of the ultrasonic wave emitting section 20 can be stabilized.

The flow channel 11 is formed by the upper plate member 14 being mounted on the lower plate member 13 to cover the U shaped groove formed in the lower plate member 13. In the present specification, the width (the length in a direction perpendicular to the drawing sheet of FIG. 1A) and the thickness (the length in the vertical direction of the drawing sheet of FIG. 1A) of the flow channel 11 are not particularly limited. However, the width is within a range from 1 mm to 10 mm, and the thickness is within a range from 50 μm to 2 mm.

The sensor portion 15 is formed at the first predetermined region on the wall surface of the flow channel 11. In addition, the sensor portion 15 is constituted by the metal film 16 and the immobilized antibodies B1. A single sensor portion 15 or a plurality of sensor portions 15 may be provided. A plurality of antigens can be detected in the case that a plurality of sensor portions having different types of immobilized antibodies B1 immobilized thereon are provided, thereby enabling multiple item array analysis and measurement. It is preferable for detection of signal light to be performed after the liquid sample reaches the sensor portion and sufficiently pervades the sensor portion, from the viewpoint of measurement sensitivity.

The detecting method may be combined with a highly sensitive analysis method that utilizes an enhancing field Ew formed by plasmon generated on the metal film 16, by the metal film 16 being included in the sensor portion 15. For example, in the case that the metal film 16 is a solid film formed by a metallic material, the surface plasmon resonance method, the surface plasmon enhanced fluorometry method, or the SPCE (Surface Plasmon Coupled Emission) method may be utilized. In the case that the metal film 16 is a layer formed by fine metal particles, the local surface plasmon resonance method may be utilized. The material of the metal film 16 is not particularly limited. Examples of materials which are desirable from the viewpoint of inducing plasmon include Au, Ag, Cu, Pt, Ni, and Ti. Among these, Au and Ag, which exhibit high electric field enhancing effects, are particularly preferred. It is desirable for the thicknesses of the metal film 16 to be determined such that surface plasmon is strongly excited, taking the material of the metal film 16 and the wavelength of the measuring light beam Le into consideration. For example, in the case that a laser beam having a central wavelength of 780 nm is employed as the measuring light beam Le, and Au is employed as the material of the metal film 16, a favorable thickness of the metal film 16 is 50 nm±5 nm.

The immobilized antibodies B1 are antibodies that specifically bind with the antigens A. The type of antibody is not particularly limited, and may be selected according to detection conditions (particularly the type of antigen the antigen A is). For example, in the case that the antigens A are hCG antigens (molecular weight: 38,000 Da), monoclonal antibodies that specifically bind with the antigens A may be employed as the immobilized antibodies B1. Examples of methods by which the immobilized antibodies B1 may be immobilized onto metal film 16 include physical adsorption, and immobilization by static electricity or by chemical bonds after introducing functional groups such as carboxyl groups, amino groups, and thiol groups onto the acoustic matching layer by surface modifications.

The acoustic absorber 17 is provided at the predetermined portion of the flow channel member 12 corresponding to the second predetermined region upstream of the first predetermined region along the flow channel 11. The acoustic absorber may be provided at the first predetermined region and/or the predetermined portion of the flow channel 12 corresponding to the second predetermined region. In the present specification, the predetermined portion of the flow channel member 12 corresponding to the predetermined region of the wall surface of the flow channel 11 refers to a predetermined portion of the flow channel member 12 having a surface which is the predetermined region, and has a projection range that overlaps the predetermined region in plan view (from a viewpoint from the upper direction in the drawing sheet of FIG. 1A). For example, in the present embodiment, an acoustic matching layer 18a is provided at a portion of the predetermined portion of the flow channel member 12 that corresponds to the second predetermined region. In addition, in the present specification, that a certain element is provided at a predetermined portion of the flow channel member 12 corresponding to a predetermined region on the wall surface of the flow channel 11 means that the element is provided to contact the predetermined portion, or that the element itself constitutes the predetermined portion. That is, in the latter case, the element is a portion of the flow channel member 12. The acoustic absorber 17 absorbs the ultrasonic waves U which are emitted in a direction that traverses the flow channel 11 and prevents the ultrasonic waves U from being reflected back toward the flow channel 11. Thereby, generation of ultrasonic wave components that propagate unidirectionally from the ultrasonic wave emitting section 20 toward the acoustic absorber 17 is facilitated. The material of the acoustic absorber is not particularly limited, but it is preferable for the acoustic attenuation coefficient to be 1 dB/cm or greater, and more preferably 5 dB/cm or greater. A specific preferable material for the acoustic absorber is urethane. The thickness of the acoustic absorber 17 is not particularly limited, as long as the acoustic absorber 17 is capable of sufficiently absorbing the ultrasonic waves U. For example, if the frequency of the ultrasonic waves U is 100 kHz, urethane foam is the material of the acoustic absorber 17, and the thickness of the acoustic absorber 17 is set to 3.0 cm, attenuation will be 7 dB.

The part of the flow channel member 12 between the acoustic absorber 17 and the flow channel and the part of the flow channel member between the ultrasonic wave emitting section 20 and the flow channel 11 are acoustic matching layers 18a and 18b, respectively. By providing the acoustic matching layers 18a and 18b, reflection of ultrasonic waves that propagate from the ultrasonic wave emitting section 20 to the acoustic absorber 17 between the ultrasonic wave emitting section 20 and the acoustic absorber 17 can be prevented.

The acoustic matching layers 18a and 18b are layers that function to match the acoustic impedance (Z: Z=c (speed of sound within a substance)×ρ (the density of the substance)) of the flow channel and the liquid sample S which is supplied into the flow channel 11. Therefore, the acoustic matching layers 18a and 18b are formed by a material with an acoustic impedance equivalent to the acoustic impedance of the liquid sample S. That is, the acoustic impedance values of the acoustic matching layers are set appropriately according to the acoustic impedance value of the liquid sample S. More specifically, it is preferable for the acoustic impedance values of the acoustic matching layers to be set such that the components of the ultrasonic waves that pass through the interfaces between the acoustic matching layers and the liquid sample S to be greater than 0% of the components of the ultrasonic waves that enter the interfaces. If the components that pass through the interfaces are greater than 0% of the components that enter the interfaces, the amount of components of the ultrasonic waves U that propagate from the ultrasonic wave emitting section 20 to the acoustic absorber 17 through the flow channel 11 will increase, and the advantageous effects of the present invention can be obtained.

For example, commonly, water ($Z=1.48\times10^6$ $N \cdot s \cdot m^{-3}$ (at room temperature)) is utilized as a solvent in cases that biological substances are analyzed. Therefore, in the case that a liquid sample S having an acoustic impedance equivalent to that of water is utilized, it is necessary for the acoustic impedance values of the acoustic matching layers to be within a range from 0.2 to $8.8\times10^6$ $N \cdot s \cdot m^{-3}$ (at room temperature), in order for 50% or more of the components of ultrasonic waves to pass through the interfaces. In such cases, specific preferred examples of the material of the acoustic matching layers 18a and 18b include: soft polyethylene ($Z=1.75\times10^6$ $N \cdot s \cdot m^{-3}$ (at room temperature)), polystyrene ($Z=2.48\times10^6$ $N \cdot s \cdot m^{-3}$ (at room temperature)) and rubber materials. Silicone rubbers such as PDMS (polydimethylsiloxane), natural rubber ($Z=1.50\times10^6$ $N \cdot s \cdot M^{-3}$ (at room temperature)), and styrene-butadiene rubber ($Z=1.76\times10^6$ N·s·m$^{-3}$ (at room temperature)) are more preferable. PDMS ($Z=1.06\times10^6$ N·s·m$^{-3}$ (at room temperature)) is particularly preferable, from the viewpoint of ease in shaping and controlling the thickness of the layer. Meanwhile, it would be easy for those skilled in the art to derive an appropriate range of acoustic impedance values that would result in 50% or more of the components of ultrasonic waves to pass through the interfaces and to select a material suited for the acoustic matching layers, even in the case that the acoustic impedance value of the liquid sample S is different from that of water.

The ultrasonic wave emitting section is provided at a predetermined portion corresponding to a predetermined region of the wall surface of the flow channel 11 that faces the second predetermined region such that the ultrasonic waves U can be emitted toward the acoustic absorber 17 so as to traverse the flow channel 11. In the present embodiment, the ultrasonic wave emitting section 20 is provided such that the ultrasonic waves U propagate in a direction perpendicular to the longitudinal direction of the flow channel 11. However, it is not necessary for the ultrasonic wave emitting section 20 to be provided such that the ultrasonic waves U propagate perpendicular to the longitudinal direction of the flow channel 11. It becomes possible to generate ultrasonic waves U that propagate from the ultrasonic wave emitting section 20 to the acoustic absorber 17, by providing the ultrasonic wave emitting section 20. Note that in the present specification, "ultrasonic waves U that propagate" refers to ultrasonic waves which are not in the state of standing waves. In addition, the "ultrasonic wave emission region" at which ultrasonic wave emission is possible refers to a spatial region within the flow channel 11, at which substances within the flow channel 11 can receive the operation of force due to radiant pressure of the ultrasonic waves U when the ultrasonic wave emitting section 20 emits the ultrasonic waves U toward the acoustic absorber 17 so as to traverse the flow channel 11.

The ultrasonic wave emitting section 20 is constituted by an ultrasonic wave transducer, for example. Ultrasonic wave transducers are piezoelectric elements formed by piezoelectric ceramics, or by polymeric molecular films such as polyvinyl pyrolidone. PZT-Pb (Zr.Ti) O3 type Soft Material C-82 (by Fuji Ceramics) is a preferred ultrasonic wave transducer. In the present embodiment, the ultrasonic wave emitting section 20 is constituted by a single ultrasonic wave emitting element (an ultrasonic transducer, for example). However, the ultrasonic wave emitting section 20 may be constituted by two or more ultrasonic wave emitting elements. The ultrasonic wave emitting section 20 may be formed as a portion of the surface of the wall of the flow channel such that it directly contacts the liquid sample S within the flow channel. However, taking the fact that the apparatus will be used repeatedly into consideration, it is preferable for the ultrasonic wave emitting section 20 emit ultrasonic waves into the flow channel 11 through the flow channel member 12.

The frequency of the ultrasonic waves can be set as appropriate according to the length of the flow channel 11 in the direction in which the ultrasonic waves are emitted. Specifically, the frequency of the ultrasonic waves U is determined as follows. In the case that substances are moved by force exerted by radiant pressure of propagating ultrasonic waves U, a pressure distribution must be present in the propagating direction of the ultrasonic waves U. That is, in the case that the wavelength of the ultrasonic waves U is too large (that is, the frequency is too small) with respect to the length in the propagating direction (the thickness of the flow channel 11), hardly any pressure distribution is generated, and therefore substances cannot be moved. Accordingly, the lower limit of the frequency of the ultrasonic waves is determined according to the relationship with the thickness of the flow channel 11. For example, in the case that the ultrasonic waves U propagate through the flow channel 11 which has a thickness of 1 mm, the frequency at which one wavelength of the ultrasonic waves U can propagate through the flow channel is 1500 (m/s)/($1\cdot10^{-3}$(m))=1.5 MHz. Meanwhile, the force imparted by the radiant pressure of the propagating ultrasonic waves U is proportionate to the frequency of the ultrasonic waves, because the absorption coefficient α of the ultrasonic waves. Accordingly, a greater force operates as the frequency of the ultrasonic waves W becomes higher. Therefore, it is preferable for the frequency of the ultrasonic waves U to be higher from the viewpoint of substance movement. However, if the wavelength of the ultrasonic waves U becomes approximately the same as the size of the substances that receive the operation of the aforementioned force, pressure distributions will be generated within the substances. For this reason, in the case that blood cells are detection target substances, for example, the possibility that the substances will be damaged will become high. Accordingly, the upper limit of the frequency of the ultrasonic waves U is determined according to the relationship with the size of the detection target substance. For example, in the case that the detection target substance is human red blood cells (size: approximately 8 μm), the wavelength of the ultrasonic waves U will be 8 μm when the frequency is 190 MHz, assuming that the speed of sound is 1500 m/s.

The ultrasonic wave control section 21 controls the ultrasonic wave emitting section 20. The ultrasonic wave control section 21 may be a separate unit equipped with a power source, an ultrasonic wave generating circuit, a modulating circuit, and an output circuit. In addition, the ultrasonic wave control section 21 may be further equipped with additional circuits, such as a circuit for freely forming the waveform of the ultrasonic waves as necessary. A multifunction generator WF1974 (by NF Corporation) may be employed as the ultrasonic wave control section 21, for example. The waveform of the drive voltage may be any desired shape, such as a sine wave, a rectangular wave, a triangular wave, and a ramp wave. The ultrasonic wave emitting section 20 and the ultrasonic wave control section 21 function as the ultrasonic wave emitting means of the present invention.

The fluorescent labeling antibodies BF are provided in a dry state on the wall surface of the flow channel 11 upstream of the second predetermined region. The fluorescent labeling antibodies BF are constituted by modified antibodies B2 modified by fluorescent labels F. In the present embodiment, specifically, the fluorescent labeling antibodies BF are constituted by the modified antibodies B2 (modified binding substance) that specifically bind with the antigens A (detection target substance) and the fluorescent labels F (labeling substance) that modifies the antibodies B2. The combinations of the fluorescent labeling antibodies BF and the antigens A are formed by the antibodies B2 specifically binding with the antigens A. By providing the fluorescent labeling antibodies BF in a dry state within the flow channel 11, a separate operation for labeling the antigens A is obviated. The fluorescent labels F are the labeling substance of the present invention. The labeling substance is not particularly limited, and fluorescent pigment molecules, fluorescent particles, metal particles, quantum dots, metallic core shell particles, etc., may be employed. It is preferable for solid, rigid labeling particles to be employed, such that the force of the radiant pressure of the propagating ultrasonic waves U operate effectively on the fluorescent labels. Examples of such labeling particles include the aforementioned fluorescent particles, metal particles, and quantum dots. Here, the fluorescent particles refer to particles constituted by polystyrene particles and a plurality of fluorescent pigment molecules, quantum dots, or the like enveloped in the polystyrene particles. The particles that envelop the fluorescent pigment and the like therein need only to have light transmitting properties. Polyethylene particles and $SiO_2$ particles may be utilized instead of polystyrene particles. It is preferable for the size of the labeling particles to be within a range from 0.05 µm to 10 mm, and more preferably 0.1 µm to 1 mm, because the force applied by the radiant pressure of the ultrasonic waves U is proportionate to the volumes of substances, and from the viewpoint of dispersion speed. Although labeling is performed within the flow channel 11 after the sample is supplied to the flow channel in the present embodiment, the timing at which the antigens A are labeled is not particularly limited. The antigens A may be caused to react with the labels prior to the sample being supplied to the flow channel 11.

The light source 22 may be a laser light source and is not particularly limited, but rather may be selected as appropriate according to detection conditions. As described previously, the light source 22 is arranged such that the measuring light beam Le output thereby enters the interface between the flow channel member 12 and the metal film 16 of the sensor chip C1 at a resonance angle that causes total reflection of the measuring light beam Le at the interface, such that surface plasmon resonance occurs at the metal film 16. Note that it is preferable for the measuring light beam Le to be P polarized light, such that surface plasmon can be induced. The timing at which the measuring light beam Le is emitted is not particularly limited.

The photodetector 23 detects the fluorescence Lf generated by the fluorescent labels F. Examples of photodetectors to be employed as the photodetector 23 include: CCD's; PD's (photodiodes); photomultipliers; and c-MOS's. It is preferable for a cooled CCD to be employed from the viewpoint of detection sensitivity.

Hereinafter, the procedures by which an assay is performed according to the sandwich method to detect whether the antigen A, which is a detection target substance, is included in a whole blood sample S by the detection target substance detecting method of the present embodiment using the detecting apparatus 1 will be described with reference to FIG. 2.

Step 1: The whole blood sample S, which is the target of inspection, is caused to flow into the detecting chip C1 through the flow inlet 14a.

Step 2: After the whole blood sample S is caused to flow into the flow channel 11, the ultrasonic wave emitting section 20 emits ultrasonic waves U toward the acoustic absorber 17 in a direction that traverses flow channel 11, to generate the ultrasonic waves U that propagate within the flow channel 11.

Step 3: The sample S seeps out into the channel 11 by capillary action. The whole blood sample and the fluorescent labeling antibodies BF (the fluorescent particles F modified with the antibodies B2) mix, the antigens A within the sample S bind with the labeling secondary antibodies BF, and the sample flows further along the flow channel 11. A pump may be connected to the air opening 14b, and the whole blood sample S may be caused to flow by suctioning and extruding operations of the pump, in order to expedite reactions and to shorten detection time.

Step 4: The fluorescent labeling antibodies BF which are bound to the antigens A pass through the ultrasonic wave emission region. At this time, forces exerted by radiant pressure of the propagating ultrasonic waves U operate on the fluorescent labeling antibodies BF, and the fluorescent labeling antibodies BF are moved toward the direction of the second predetermined region on the wall surface of the flow channel. As a result, the fluorescent labeling antibodies BF become concentrated in the vicinity of the second predetermined region.

Step 5: the sample S gradually flows along the flow channel 11 toward the air opening 14b, and the antigens A, which are bound to the labeling secondary antibodies BF, bind with the immobilized antibodies B1, which are immobilized onto the sensor portion 15. So called sandwich configurations, in which the antigens A are sandwiched between the immobilized antibodies B1 and the labeling antibodies BF, are formed.

Step 6: Even in the case that the labeling antibodies BF which were not immobilized onto the sensor portion 15 remain on the sensor portion 15, the following sample S functions as a cleansing agent that washes the labeling antibodies BF, which are floating or non specifically adsorbed onto the sensor portion 15, away. The sample S which has passed over the sensor portion 15 is collected in a waste liquid reservoir 11b.

The antigens A can be detected by irradiating the measuring light beam be onto the sensor portion 15 and then detecting fluorescence Lf emitted by the fluorescent labels F after performing the above steps.

Hereinafter, the advantageous effects of the present embodiment will be described in detail.

In an assay method, in which one substance (immobilized antibodies B1) of a pair of immune substances is immobilized onto the two dimensional sensor portion 15, and the specific properties of the reactions are utilized to detect the other substance (antigens A) of the pair of immune substance, to qualitatively or quantitatively analyze the amount of the other substance (antigens A), the speed of the aforementioned reactions is expressed by the Langmuir adsorption formula shown below.

$$\frac{d\theta}{dt} = k_a C(1-\theta) - k_d \theta \qquad \text{Formula (1)}$$

wherein $\theta$ is the percentage of the number of sites (number of immobilized antibodies B1 which have bound with the antigens A) that the antigen A (detection target substance) have bound to, with respect to the number of sites (number of immobilized antibodies B1) which are capable of binding with the antigens A (detection target substance) on the sensor portion 15. That is, $\theta$ represents the percentage of the sensor portion 15 occupied by the antigens A. $k_a$ and $k_d$ respectively represent a binding speed coefficient and a disassociation speed constant, which depend on the immune substances. C represents the concentration of the antigens A (detection target substance) within the liquid sample.

In the assay method described above, improving reaction speeds means increasing the value of $d\theta/dt$. If the constant $k_a$ is increased and the constant $k_d$ is decreased in the formula above, the reaction speed can be improved. However, these constants are determined by the immune substances that react with each other, and therefore are physical quantities that cannot be improved after selecting the immune substances. Meanwhile, as the antigens A bind to the sensor portion 15, the concentration C of the antigens within the liquid sample S decreases. Therefore $d\theta/dt$, and consequently, the reaction speed, decreases. If the liquid sample S is supplied before the concentration C decreases due to the aforementioned binding by causing the liquid sample S to flow through a flow channel, the decrease in concentration can be prevented, and reaction speed can be maintained. That is, the reaction speed being controlled by dispersion can be prevented by causing the liquid sample S to flow. However, even if the reaction speed being controlled by dispersion can be prevented, the reaction speed is determined by the antigen concentration C of the supplied liquid sample S, and therefore, further improvements in reaction speed cannot be expected. Therefore, the present invention emits the ultrasonic waves U toward the acoustic absorber 17 in a direction that traverses the flow channel 11 to move the antigens A expediently and efficiently onto the sensor portion 15 by the forces imparted by the radiant pressure of the propagating ultrasonic waves U. The antigens A become concentrated on the sensor portion 15, to effectively increase the antigen concentration C. Thereby, the percentage of occupation θ is greatly increased within a short period of time even if a liquid sample S having a low antigen concentration C is employed, and signals sufficiently greater than noise signals, such as apparatus noise including dark current, can be detected. Accordingly, expedient analysis and measurement at high sensitivity can be achieved.

The above force operates in the direction that the ultrasonic waves U propagate, and the intensity $F_0$ of the force is proportionate to the volume V of the substance that the force operates on and the ultrasonic wave absorption coefficient α of the substance, as shown in Formula (2) below.

$$F_0 = 2\alpha VI/c_0 \quad \text{Formula (2)}$$

wherein $F_0$ is the intensity of the force imparted by radiant pressure of the propagating ultrasonic waves U, I is the intensity of the ultrasonic waves U that operate on the substance, and $c_0$ is the speed of sound within a medium.

In assays performed according to the sandwich method, in the case that the antigens A are labeled prior to being immobilized onto the sensor portion 15, reactions are divided into two steps. The first step includes primary reactions, in which the antigens A are caused to react with the labeling antibodies BF, and the second step includes secondary reactions, in which the combinations of the labeling antibodies BF and the antigens A are caused to react with the immobilized antibodies B1. Because the primary reactions are performed between the antigens A and the labeling antibodies BF within the liquid sample S, which has a sufficiently high concentration of the labeling antibodies BF, the reaction efficiency is favorable, and approximately 90% or more of the antigens A bind with the labeling antibodies BF within a short amount of time. In contrast, the secondary reactions are reactions between the antigens A of the aforementioned combinations within the liquid sample S and the immobilized antibodies B1 on the two dimensional planar sensor portion 15, the reaction efficiency is low, and the binding rate is several % or less. For this reason, it is extremely important to improve the reaction efficiency of the secondary reactions. The transport and concentration of the combinations (the antigens A) on the sensor portion 15 realized by the present invention exhibits extremely great advantageous effects.

Further, the present invention utilizes propagating ultrasonic waves. Therefore, the method of the present invention is much more simple than the method that generates standing waves within a flow channel disclosed in U.S. Patent Application Publication No. 20090169428.

As described above, the detection target substance detecting method of the present embodiment employs the detecting chip equipped with the flow channel member having the flow channel through which the liquid sample flows, the sensor portion, and the acoustic absorber. The liquid sample and an amount of the labeling binding substance that contains the labeling substance, which is immobilized onto the sensor portion, corresponding to the amount of the detection target substance are caused to flow in the flow channel. When the liquid sample passes through the ultrasonic wave emission region at which ultrasonic waves can be emitted, ultrasonic waves are emitted toward the acoustic absorber in a direction perpendicular to the longitudinal direction of the flow channel. The measuring light beam is emitted onto the sensor portion, and signal light generated by the labeling substance due to the emission of the measuring light beam is detected. The amount of the labeling binding substance immobilized on the sensor portion is measured based on the amount of the detected signal light, to detect the detection target substance. Because the ultrasonic wave is emitted toward the acoustic absorber that absorbs ultrasonic waves in the direction perpendicular to the longitudinal direction of the flow channel, forces imparted by radiant pressure of the ultrasonic waves act on substances within the flow channel. As a result, expedient and sensitive detection of the detection target substance becomes possible in target substance detection that detects a detection target substance at a sensor portion provided in a flow channel.

Further, the detection target substance detecting chip of the present embodiment comprises the flow channel member having the flow channel through which the liquid sample that may contain the detection target substance is caused to flow, the flow inlet through which the liquid sample is caused to flow into the flow channel, and the air opening for causing the liquid samples which have flowed in through the flow inlet to flow into the flow channel; the sensor portion formed at the first predetermined region on the wall surface of the flow channel, at which the immobilized binding substance that specifically binds with the detection target substance is immobilized; and the acoustic absorber provided at the first predetermined region and/or at the predetermined portion corresponding to the second predetermined region upstream of the first predetermined region along the flow channel. The above detection target substance detecting method can be executed by the chip having this configuration. As a result, expedient and sensitive detection of the detection target substance becomes possible in target substance detection that detects a detection target substance at a sensor portion provided in a flow channel.

Further, the detection target substance detecting apparatus of the present embodiment comprises: the detection target substance detecting chip comprising the flow channel member having the flow channel through which the liquid sample that may contain the detection target substance is caused to flow, the flow inlet through which the liquid sample is caused to flow into the flow channel, and the air opening for causing the liquid samples which have flowed in through the flow inlet to flow into the flow channel; the sensor portion formed at the first predetermined region on the wall surface of the flow channel, at which the immobilized binding substance that specifically binds with the detection target substance is immobilized; and the acoustic absorber provided at the first predetermined region and/or at the predetermined portion corresponding to the second predetermined region upstream of the first predetermined region along the flow channel; the ultrasonic wave emitting means provided on the flow channel member that emits ultrasonic waves toward the acoustic absorber in a direction perpendicular to the longitudinal direction of the flow channel; the light emitting means for emitting the measuring light beam onto the sensor portion; and the photodetector for detecting the signal light generated at the sensor portion due to emission of the measuring light beam. The above detection target substance detecting method can be executed by the apparatus having this configuration.

As a result, expedient and sensitive detection of the detection target substance becomes possible in target substance detection that detects a detection target substance at a sensor portion provided in a flow channel.

<Design Modifications to the First Embodiment>

Figure 3A:
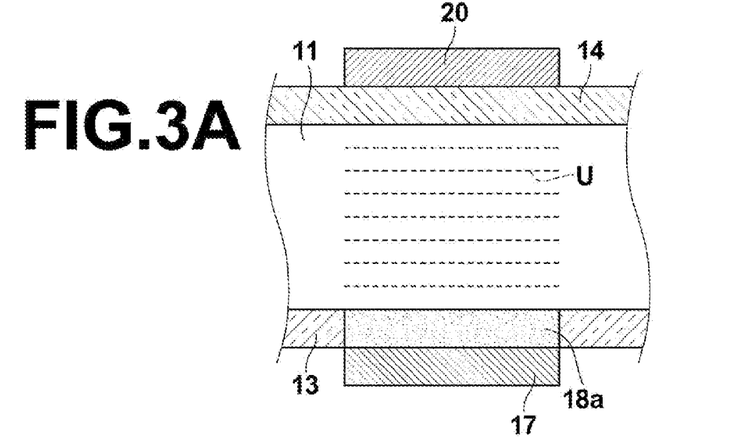
FIG. 3A is a schematic sectional diagram that illustrates an example of a design modification to the ultrasonic wave emitting section of the first embodiment.

In the first embodiment, the acoustic matching layers 18a and 18b were respectively provided at the portion between the acoustic absorber 17 and the flow channel 11 and at the portion between the ultrasonic emitting section 20 and the flow channel 11. Alternatively, a configuration may be adopted, wherein only the acoustic matching layer 18a is provided at the portion between the acoustic absorber 17 and the flow channel 11, as illustrated in FIG. 3A.

Figure 3B:
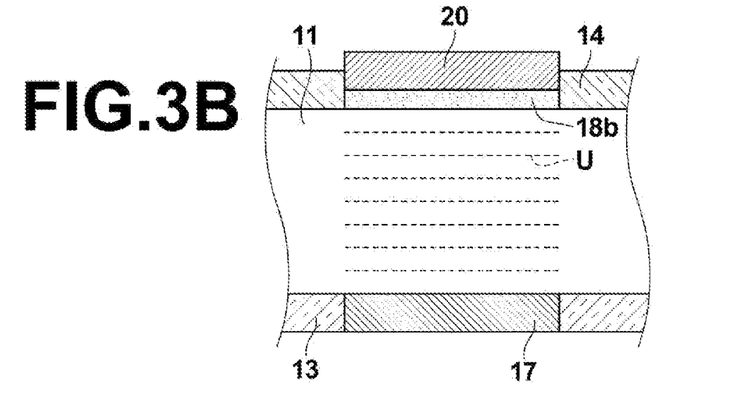
FIG. 3B is a schematic sectional diagram that illustrates an example of a design modification to an acoustic absorber of the first embodiment.

In addition, in the first embodiment, the acoustic absorber 17 was provided to correspond to the second predetermined region through the flow channel member 12. Alternatively, a configuration may be adopted, wherein the surface of the acoustic absorber 17 forms the second predetermined region, as illustrated in FIG. 3B. That is, the acoustic absorber 17 is a part of the flow channel member 12 in this case.

The first embodiment was described as a case in which the detecting apparatus 1 comprises a total reflection optical system that utilizes surface plasmon enhancement. However, the detecting apparatus 1 is not limited to such a configuration. For example, a configuration may be adopted, wherein the detecting apparatus 1 is not equipped with the metal film for inducing surface plasmon, and immobilizes the immobilized antibodies B1 onto the wall surface of the flow channel via a dielectric film (a $SiO_2$ film, for example) and a polymer film or the like. Note that in this case, the region at which the immobilized antibodies B1 are immobilized becomes the sensor portion. Further, a configuration may be adopted wherein the detecting apparatus 1 employs an incident light optical system instead of a total reflection optical system.

In the first embodiment, fluorescent labels are employed as the labels for the antigens. Alternatively, other photoresponsive labels (such as phosphorous labels, and scattered light labels) may be employed as the labels.

In addition, the first embodiment was described as a case in which the sandwich method was employed. However, the present invention may also be applied to the competition method. In this case, modified antibodies (modified binding substance) and fluorescent particles that modify the modified antibodies (modified binding substance) that specifically bind with the immobilized antibodies (immobilized binding substance) in a competitive manner with the antigens (detection target substance) are employed as the fluorescent labeling antibodies.

The first embodiment was described as a case in which antigen antibody reactions, in which antigens and antibodies are the pair of substances that specifically bind to each other, were utilized. However, the present invention exhibits the same advantageous effects in cases that protein cofactor reactions, enzyme base reactions, etc. are utilized to perform detection.

In addition, the first embodiment was described as a case in which the labeling binding substance was provided on the wall surface of the flow channel upstream of the sensor portion in a dry state. However, the present invention is not limited to such a configuration. That is, the labeling binding substance need only to be provided at a location at which it is capable of being mixed with the liquid sample in a preliminary step prior to the liquid sample reaching the sensor portion. Here, the "preliminary step" is not limited to a case in which the liquid sample and the labeling binding substance are mixed within the flow channel, and includes a case in which the liquid sample and the labeling binding substance are mixed at a location provided in the detecting chip independent of the flow channel. For example, a second flow channel may be provided in the detecting chip independent from the flow channel (a first flow channel), and the labeling binding substance may be provided on the wall surface of the second flow channel in a dry state. In this case, the liquid sample is caused to flow through the second flow channel, and then caused to flow through the first flow channel. As another example, a container portion may be provided in the flow channel member independent of the flow channel, and the labeling binding substance may be provided on the wall surface of the container portion in a dry state. In this case, the liquid sample is supplied to the container portion to mix the liquid sample and the labeling binding substance, and then the liquid sample is caused to flow through the first flow channel.

The first embodiment was described as a case in which the labeling binding substance was provided on the wall surface of the flow channel in a dry state. However, the present invention is not limited to such a configuration. For example, the labeling binding substance may be provided as part of a target substance detecting kit. Specifically, a target substance detecting kit of the present invention includes the detecting chip of the present invention and a labeling solution. The detecting chip is the same as that of the first embodiment, and comprises: a flow channel member having a flow channel through which a liquid sample that may contain a detection target substance is caused to flow, a flow inlet through which the liquid sample is caused to flow into the flow channel, and an air opening for causing the liquid samples which have flowed in through the flow inlet to flow into the flow channel; a sensor portion formed at a first predetermined region on a wall surface of the flow channel, at which an immobilized binding substance that specifically binds with the detection target substance is immobilized; and an acoustic absorber provided at the first predetermined region and/or at a predetermined portion corresponding to a second predetermined region upstream of the first predetermined region along the flow channel. Meanwhile, the labeling solution is a solution that includes the labeling binding substance that labels the detection target substance. The labeling solution is contained in a cup.

Labeling of the detection target substance in the case that the detecting kit is employed is performed by mixing the liquid sample that contains the detection target substance with the labeling solution. Mixing of the liquid sample and the labeling solution may be performed by supplying the liquid sample to the labeling solution prior to the liquid sample being caused to flow into the flow channel. Alternatively, the liquid sample and the labeling solution may be mixed within the channel by causing the liquid sample and the labeling solution to flow into the flow channel simultaneously.

[Second Embodiment]

Figure 4:
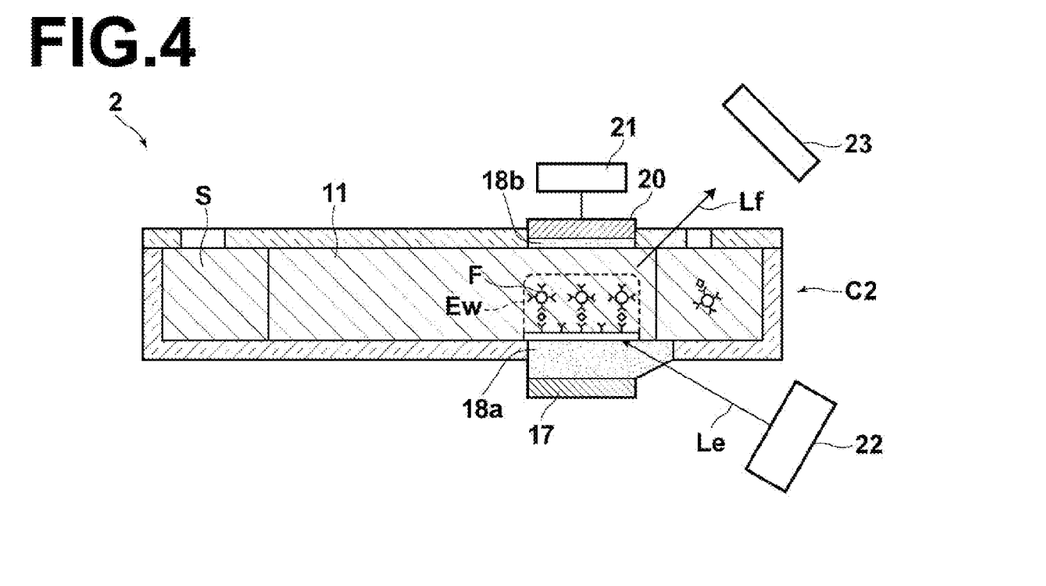
FIG. 4 is a schematic sectional diagram that illustrates a detecting apparatus employed to execute a detection target substance detecting method according to a second embodiment of the present invention.

Next, a detection target substance detecting method according to a second embodiment of the present invention will be described. FIG. 4 is a sectional view that schematically illustrates a detecting apparatus 2 which is employed in the detection target substance detecting method of the second embodiment. Note that the second embodiment will also be described as a case in which antigens and antibodies are employed as pairs of substances that specifically bind with each other, the detection target substance is an antigen, the binding substance that specifically binds with the detection target substance is an antibody, and analysis is performed by the sandwich method that employs fluorescent labels.

The detection target substance detecting method of the second embodiment mainly differs from the first embodiment in that the acoustic absorber 17 is provided at a predetermined portion of the flow channel member 12 corresponding to the first predetermined region. Accordingly, detailed descriptions of the other elements which are the same as those of the first embodiment will be omitted insofar as they are not particularly necessary.

As illustrated in FIG. 4, the detecting method of the present embodiment is executed employing the detecting apparatus 2 equipped with: a detecting chip C2; the ultrasonic wave emitting section 20 provided upstream from the sensor portion 15 that emits ultrasonic waves U toward the acoustic absorber 17 in a direction perpendicular to the longitudinal direction of the flow channel 11 through the flow channel 11; the ultrasonic wave controlling section 21 that controls the ultrasonic wave emitting section 20; the light source 22; and the photodetector 23. The detecting chip C2 includes the flow channel member 12 having the flow channel 11, the flow inlet 14a through which a liquid sample is caused to flow into the flow channel 11, and the air opening 14b for causing the liquid sample which has flowed in through the flow inlet 14a to flow into the flow channel 11; the sensor portion 15 formed at the first predetermined region on the wall surface of the flow channel 11; the acoustic absorber 17 provided at the predetermined portion of the flow channel member 12 corresponding to the first predetermined region; and the fluorescent labeling antibodies BF provided in a dry state upstream of the first predetermined region 15.

Specifically, the detecting method of the present embodiment employs the detecting apparatus 2 to cause a whole blood sample S that may contain antigens A to flow into the flow channel 11. The whole blood sample S is caused to contact the fluorescent labeling antibodies BF. When the liquid sample and the fluorescent labeling antibodies BF flow along the flow channel and pass the ultrasonic wave emission region at which emission of ultrasonic waves is enabled, the ultrasonic waves U are emitted toward the acoustic absorber 17 in a direction that traverses the flow channel 11. A measuring light beam Le is emitted toward the sensor portion 15 using the light source 22. After the whole blood sample S that flows through the flow channel 11 reaches the sensor portion 15, fluorescence Lf generated by the fluorescent labeling antibodies BF due to emission of the measuring light beam Le is detected by the photodetector 23. The amount of the fluorescent labeling antibodies BF immobilized on the sensor portion 15 is measured based on the amount of detected fluorescence Lf, to detect the antigens A. At this time, in the case that the whole blood sample S contains the antigens A, the fluorescent labeling antibodies BF bind with the antigens A, and the fluorescent labeling antibodies BF bind to immobilized antibodies B1, which are immobilized on the sensor portion 15, via the antigens A.

The acoustic absorber 17 is provided at the predetermined portion of the flow channel member 12 corresponding to the first predetermined region. In the case that the acoustic absorber 17 is provided at this location as well, substances (antigens A, fluorescent labeling antibodies BF, and combinations of the two) within the liquid sample S can be concentrated in the vicinity of the first predetermined region. However, it is preferable for the acoustic absorber 17 to be provided at the predetermined portion of the flow member 12 corresponding to the second predetermined region as in the first embodiment, from the viewpoint of efficiently concentrating substances within the liquid sample S.

In the case that the acoustic absorber 17 is provided in the manner described above, it is necessary to arrange the light source 22 and the photodetector 23 such that the sensor portion 15 will not be obscured by the acoustic absorber 17 and the ultrasonic wave emitting section 20. For example, in FIG. 4, an acoustic matching layer 18a having a greater width and thickness than that of the first embodiment is provided to facilitate entry of the measuring light beam Le into the interface between the metal film 16 and the acoustic matching layer 18a. In addition, in FIG. 4, the photodetector 23 is provided to be capable of detecting the fluorescence Lf from a direction more oblique than that of the first embodiment, to facilitate detection of the fluorescence Lf.

As described above, the detection target substance detecting method of the present embodiment also employs the detecting chip equipped with the flow channel member having the flow channel through which the liquid sample flows, the sensor portion, and the acoustic absorber. The liquid sample and an amount of the labeling binding substance that contains the labeling substance, which is immobilized onto the sensor portion, corresponding to the amount of the detection target substance are caused to flow in the flow channel. When the liquid sample passes through the ultrasonic wave emission region at which ultrasonic waves can be emitted, ultrasonic waves are emitted toward the acoustic absorber in a direction perpendicular to the longitudinal direction of the flow channel. The measuring light beam is emitted onto the sensor portion, and signal light generated by the labeling substance due to the emission of the measuring light beam is detected. The amount of the labeling binding substance immobilized on the sensor portion is measured based on the amount of the detected signal light, to detect the detection target substance. Accordingly, the present embodiment exhibits the same advantageous effects as those of the first embodiment.

Further, the detection target substance detecting chip of the present embodiment comprises the flow channel member having the flow channel through which the liquid sample that may contain the detection target substance is caused to flow, the flow inlet through which the liquid sample is caused to flow into the flow channel, and the air opening for causing the liquid samples which have flowed in through the flow inlet to flow into the flow channel; the sensor portion formed at the first predetermined region on the wall surface of the flow channel, at which the immobilized binding substance that specifically binds with the detection target substance is immobilized; and the acoustic absorber provided at the first predetermined region and/or at the predetermined portion corresponding to the second predetermined region upstream of the first predetermined region along the flow channel. Accordingly, the present embodiment exhibits the same advantageous effects as those of the first embodiment.

Further, the detection target substance detecting apparatus of the present embodiment comprises: the detection target substance detecting chip comprising the flow channel member having the flow channel through which the liquid sample that may contain the detection target substance is caused to flow, the flow inlet through which the liquid sample is caused to flow into the flow channel, and the air opening for causing the liquid samples which have flowed in through the flow inlet to flow into the flow channel; the sensor portion formed at the first predetermined region on the wall surface of the flow channel, at which the immobilized binding substance that specifically binds with the detection target substance is immobilized; and the acoustic absorber provided at the first predetermined region and/or at the predetermined portion corresponding to the second predetermined region upstream of the first predetermined region along the flow channel; the ultrasonic wave emitting means provided on the flow channel member that emits ultrasonic waves toward the acoustic absorber in a direction perpendicular to the longitudinal direction of the flow channel; the light emitting means for emitting the measuring light beam onto the sensor portion; and the photodetector for detecting the signal light generated at the sensor portion due to emission of the measuring light beam. Accordingly, the present embodiment exhibits the same advantageous effects as those of the first embodiment.

What is claimed is:

1. A detection target substance detecting method for detecting a detection target substance which may be contained in a liquid sample, comprising:

employing a detecting chip equipped with: a flow channel member having a flow channel through which the liquid sample is caused to flow; a sensor portion formed at a first predetermined region on a wall surface of the flow channel, at which an immobilized binding substance that specifically binds with the detection target substance is immobilized; and an acoustic absorber provided at least at one of a predetermined portion of the flow channel member corresponding to the first predetermined region and a predetermined portion of the flow channel member corresponding to a second predetermined region upstream of the first predetermined region along the flow channel;

causing the liquid sample and an amount of a labeling binding substance that contains a labeling substance, which is to be immobilized onto the sensor portion, corresponding to an amount of the detection target substance to flow into the flow channel;

emitting ultrasonic waves toward the acoustic absorber in a direction perpendicular to the longitudinal direction of the flow channel when the liquid sample passes through an ultrasonic wave emission region at which ultrasonic waves can be emitted;

emitting a measuring light beam onto the sensor portion;

detecting signal light generated by the labeling substance as a result of emission of the measuring light beam; and measuring the amount of the labeling binding substance immobilized onto the sensor portion based on an amount of the signal light, to detect the detection target substance.

2. The detection target substance detecting method as defined in claim 1, wherein:

the acoustic absorber is provided at a predetermined portion corresponding to the second predetermined region.

3. A detection target substance detecting chip, comprising:

a flow channel member having a flow channel through which a liquid sample that may contain a detection target substance is caused to flow, a flow inlet through which the liquid sample is caused to flow into the flow channel, and an air opening for causing the liquid sample which has flowed in through the flow inlet to flow into the flow channel;

a sensor portion formed at a first predetermined region on a wall surface of the flow channel, at which an immobilized binding substance that specifically binds with the detection target substance is immobilized;

and an acoustic absorber provided at least at one of a predetermined portion of the flow channel member corresponding to the first predetermined region and a predetermined portion of the flow channel member corresponding to a second predetermined region upstream of the first predetermined region along the flow channel.

4. The detection target substance detecting chip as defined in claim 3, further comprising:

an ultrasonic wave emission portion at which ultrasonic waves are emitted toward the acoustic absorber in a direction perpendicular to the longitudinal direction of the flow channel.

5. The detection target substance detecting chip as defined in claim 3, further comprising:

an acoustic matching layer provided at a position between the acoustic absorber and the flow channel.

6. The detection target substance detecting chip as defined in claim 4, further comprising:

an acoustic matching layer provided at least at one of a position between the acoustic absorber and the flow channel and a position between the ultrasonic wave emission portion and the flow channel.

7. The detection target substance detecting chip as defined in claim 4, wherein:

the flow channel member has a recess into which the ultrasonic wave emission portion can be fitted.

8. The detection target substance detecting chip as defined in claim 3, further comprising:

a labeling binding substance which is provided at a location where it is capable of being mixed with the liquid sample prior to the liquid sample reaching the sensor portion; wherein the labeling binding substance comprises one of a first modifying binding substance that specifically binds with the detection target substance and a second modifying binding substance that competes with the detection target substance to specifically bind with the immobilized binding substance, and a labeling substance modified by the one of the first modifying binding substance and the second modifying binding substance.

9. The detection target substance detecting chip as defined in claim 6, further comprising:

a labeling binding substance which is provided at a location where it is capable of being mixed with the liquid sample prior to the liquid sample reaching the sensor portion; wherein the labeling binding substance comprises one of a first modifying binding substance that specifically binds with the detection target substance and a second modifying binding substance that competes with the detection target substance to specifically bind with the immobilized binding substance, and a labeling substance modified by the one of the first modifying binding substance and the second modifying binding substance.

10. The detection target substance detecting chip as defined in claim 8, wherein:

the location where the labeling binding substance is capable of being mixed with the liquid sample is on the wall surface of the flow channel upstream of the second predetermined region.

11. The detection target substance detecting chip as defined in claim 9, wherein:

the location where the labeling binding substance is capable of being mixed with the liquid sample is on the wall surface of the flow channel upstream of the second predetermined region.

12. The detection target substance detecting chip as defined in claim 8, wherein:

the location where the labeling binding substance is capable of being mixed with the liquid sample is a second flow channel provided in the flow channel member independent of the flow channel.

13. The detection target substance detecting chip as defined in claim 9, wherein:

the location where the labeling binding substance is capable of being mixed with the liquid sample is a second flow channel provided in the flow channel member independent of the flow channel.

14. The detection target substance detecting chip as defined in claim 8, wherein:
the location where the labeling binding substance is capable of being mixed with the liquid sample is a container portion provided in the flow channel member independent of the flow channel.

15. The detection target substance detecting chip as defined in claim 9, wherein:
the location where the labeling binding substance is capable of being mixed with the liquid sample is a container portion provided in the flow channel member independent of the flow channel.

16. A detection target substance detecting kit, comprising:
the detection target substance detecting chip defined in claim 3; and
a labeling solution that includes a labeling binding substance for labeling the detection target substance; the labeling binding substance comprising one of a first modifying binding substance that specifically binds with the detection target substance and a second modifying binding substance that competes with the detection target substance to specifically bind with the immobilized binding substance, and a labeling substance modified by the one of the first modifying binding substance and the second modifying binding substance.

17. A detection target substance detecting apparatus to be utilized in a detection target substance detecting method that employs the detection target substance detecting chip defined in claim 3, comprising:
ultrasonic wave emitting means for emitting ultrasonic waves toward the acoustic absorber in a direction perpendicular to the longitudinal direction of the flow channel;
light emitting means for emitting a measuring light beam to the sensor portion; and
a photodetector for detecting signal light generated at the sensor portion due to the measuring light beam being emitted thereon.

* * * * *